US012653622B2

(12) United States Patent
Biedermann et al.

(10) Patent No.: US 12,653,622 B2
(45) Date of Patent: Jun. 16, 2026

(54) SURGICAL DEVICE FOR USE IN SPINAL OR MUSCULOSKELETAL SURGERY OR IN SIMULATED SURGERY AND METHOD OF USING THE SAME

(71) Applicant: BIEDERMANN TECHNOLOGIES GMBH & CO. KG, Donaueschingen (DE)

(72) Inventors: Timo Biedermann, Trossingen (DE); Dimosthenis Dandanopoulos, VS-Schwenningen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 437 days.

(21) Appl. No.: 18/063,236

(22) Filed: Dec. 8, 2022

(65) Prior Publication Data

US 2023/0172669 A1 Jun. 8, 2023

Related U.S. Application Data

(60) Provisional application No. 63/287,279, filed on Dec. 8, 2021.

(30) Foreign Application Priority Data

Dec. 8, 2021 (EP) .................................... 21213260

(51) Int. Cl.
*A61B 34/20* (2016.01)
*A61B 34/10* (2016.01)

(52) U.S. Cl.
CPC .............. *A61B 34/20* (2016.02); *A61B 34/10* (2016.02); *A61B 2034/101* (2016.02);
(Continued)

(58) Field of Classification Search
CPC ... A61B 34/20; A61B 34/10; A61B 2034/101; A61B 2034/2051; A61B 2034/2055;
(Continued)

(56) References Cited

U.S. PATENT DOCUMENTS 9,517,092 B2 12/2016 Biedermann et al.
2008/0200794 A1* 8/2008 Teichman .............. A61B 90/39
600/407

(Continued)

FOREIGN PATENT DOCUMENTS

EP 2 719 347 A1 4/2014
WO WO 2021/160845 A1 8/2021

OTHER PUBLICATIONS

Extended European Search Report for Application No. 21213260.9, mailed Sep. 23, 2022, 20 pages.

*Primary Examiner* — Bo Joseph Peng
(74) *Attorney, Agent, or Firm* — Womble Bond Dickinson (US) LLP

(57) ABSTRACT

A device for use in spinal surgery or musculoskeletal surgery, or in simulated surgery, where the device is non-implantable, includes a first component having a first end, a second end, and a longitudinal axis extending between the first and second ends, wherein the first end is connectable to a second component in an adjustable manner, and a detection device configured to monitor position changes of the second component relative to the first component and to deliver position data corresponding to the position changes to an evaluation unit that is separate from the device. At least part of the detection device at or near the first end of the first component is movable laterally away from the longitudinal axis to monitor movement of at least part of the second component away from the longitudinal axis.

20 Claims, 13 Drawing Sheets

(52) U.S. Cl.
CPC ................. *A61B 2034/2051* (2016.02); *A61B 2034/2055* (2016.02); *A61B 2034/2059* (2016.02)

(58) Field of Classification Search
CPC ........ A61B 2034/2059; A61B 17/1604; A61B 17/1615; A61B 17/1671; A61B 17/8635; A61B 17/864; A61B 17/8875; A61B 2017/00221; A61B 2034/2048; A61B 2090/0811; G09B 23/285; A61F 2002/30556; A61F 2002/4628; A61F 2/4465; A61F 2002/4627; A61F 2/4611
See application file for complete search history.

(56) References Cited

U.S. PATENT DOCUMENTS

| | | | |
|---|---|---|---|
| 2014/0172105 A1 | 6/2014 | Frasier et al. | |
| 2017/0056194 A1 | 3/2017 | Biedermann et al. | |
| 2017/0209286 A1 | 7/2017 | Palmatier et al. | |
| 2019/0247102 A1 | 8/2019 | Biedermann | |
| 2019/0377432 A1* | 12/2019 | Gogarty ............... | G06F 3/0325 |
| 2019/0380794 A1 | 12/2019 | Al Jewad et al. | |
| 2019/0388161 A1* | 12/2019 | Cicchini ................ | A61B 90/11 |
| 2021/0077270 A1 | 3/2021 | Biedermann | |

* cited by examiner

SURGICAL DEVICE FOR USE IN SPINAL OR MUSCULOSKELETAL SURGERY OR IN SIMULATED SURGERY AND METHOD OF USING THE SAME

CROSS-REFERENCE TO RELATED APPLICATION(S)

The present application claims priority to and the benefit of U.S. Provisional Patent Application No. 63/287,279, filed Dec. 8, 2021, the contents of which are hereby incorporated by reference in their entirety, and claims priority from European Patent Application EP 21 213 260.9, filed Dec. 8, 2021, the contents of which are hereby incorporated by reference in their entirety.

BACKGROUND

Field

The application relates to a surgical device, in particular, for use in spinal or musculoskeletal surgery or in simulated surgery, and a method of using the same. More specifically, the application relates to a surgical implant, in particular, for use in spinal or musculoskeletal surgery, and to a system including such a surgical implant and an instrument for inserting the surgical implant. The application also concerns a method for simulating the insertion of the surgical implant into a body using the instrument.

Description of Related Art

Instruments for use in spinal or musculoskeletal surgery that include a sensor for detecting specific conditions are known in the art. For example, US 2019/0247102 A1 describes a cannulated bone anchor with an elongate instrument in the form of a sensor with a sensor element at the tip that extends through the channel of the bone anchor and that is configured to sense respective characteristics such as, for example, the density of the bone, or which is configured to perform neuro-monitoring. Another instrument that is configured to detect a position of a first member relative to a second member of the instrument is known from U.S. Pat. No. 9,517,092 B2.

Lumbar or thoracic interbody fusion surgery is one of the most commonly performed spinal fusion surgeries using an instrument. Some known surgical approaches for interbody fusion of the lumbar spine include posterior lumbar interbody fusion (PLIF), transforaminal lumbar interbody fusion (TLIF), anterior lumbar interbody fusion (ALIF), antero-lateral ALIF, and lateral interbody fusion. The transforaminal lumbar interbody fusion technique involves approaching the spine from the side of the spinal canal through a midline incision in the patient's back. The implant is inserted between adjacent vertebra along a curved trajectory. This is enabled by the intervertebral implant being pivotable or rotatable around an axis of rotation relative to a longitudinal axis of the instrument for inserting the intervertebral implant. Intervertebral implants that may be suitable are described, for example, in US 2017/0056194 A1 and US 2021/0077270 A1.

Monitoring of surgical steps in a patient's body during surgery has become an important aid for facilitating and improving surgery. Meanwhile, there also exist methods and arrangements for simulating orthopedic spinal column surgery. WO 2021/160845 A1 describes a method using model structures which form anatomical structures and which are optically, haptically, and functionally modeled based on organs or organ parts to be surgically treated. By means of the model structures, simulated surgical operations are carried out.

However, monitoring of surgical steps that include non-axial movements of a component are difficult.

SUMMARY

It is an object of the invention to provide an improved or alternative surgical device, in particular for spinal or musculoskeletal surgery or for simulated surgery, and a method of using the same, as well as a surgical implant and a system including such a surgical implant and an instrument for inserting the surgical implant, that are suitable for monitoring, in particular, computer-based monitoring, of the surgical insertion steps. Moreover, it is an object of the invention to provide a method for simulating the implant insertion.

A device for use in spinal or musculoskeletal surgery or in simulated surgery includes a first component, a second component that is configured to assume various positions relative to the first component, and a detection device configured to detect a position of the second component relative to the first component, wherein the detection device is configured to deliver position data corresponding to detected positions of the second component to an evaluation unit for monitoring a change of the position of the second component relative to the first component.

The surgical implant and the system is particularly suitable for navigated surgery. In navigated surgery, the position of the implant to be inserted and/or the instrument for inserting the implant is tracked via optical or electromagnetic methods and shown on images of the patient, such as conventional X-ray images or computer tomography (CT). In particular, the surgical device and the method permit real-time visualization of the insertion process of the implant or of a manipulation process during the surgery by utilizing computer-aided navigation.

The term surgical implant or implant as described hereinafter includes not only a surgical implant that is intended to be inserted and to remain in a patient's body, but also includes trial implants that are used for testing and that do not remain in the patient's body or that are not implanted in a live body at all, or further includes instruments or portions thereof that are temporarily inserted and removed afterwards, such as an awl or a drill.

In the case that the surgical implant is an intervertebral implant, it is possible to track a curved insertion trajectory, in particular in transforaminal lumbar interbody fusion techniques. However, the intervertebral implant can also be used for other fusion techniques.

Generally, intervertebral implants, for example, implants according to US 2017/0056194 A1 and US 2021/0077270 A1, the disclosures of which are incorporated herein by reference, may be used for the surgical implant that is provided with the detection device.

In a further embodiment, the instrument may be provided with a navigation device for optical or electrical detection of a position of the instrument relative to a reference position. Hence, with the surgical implant and the instrument, it is possible to monitor the surgical steps from the beginning of insertion until the final placement of the implant in a patient's body.

An embodiment of a method of a surgical procedure using a surgical device as described above includes a step of detecting positions of the second component relative to the first component and using the position data corresponding to the detected positions for computer-aided navigation.

The method can be carried out using a model of a patient's body part in which the surgery is intended to be carried out and which may have similar properties compared to a live body. In this case, the method is a simulation method of a surgical procedure. Alternatively, the method can be carried out on a cadaver as well as on a live body.

BRIEF DESCRIPTION OF THE DRAWINGS

Further features and advantages of the invention will become apparent from the description of embodiments by means of the accompanying drawings. In the drawings.

DETAILED DESCRIPTION

Figure 1:
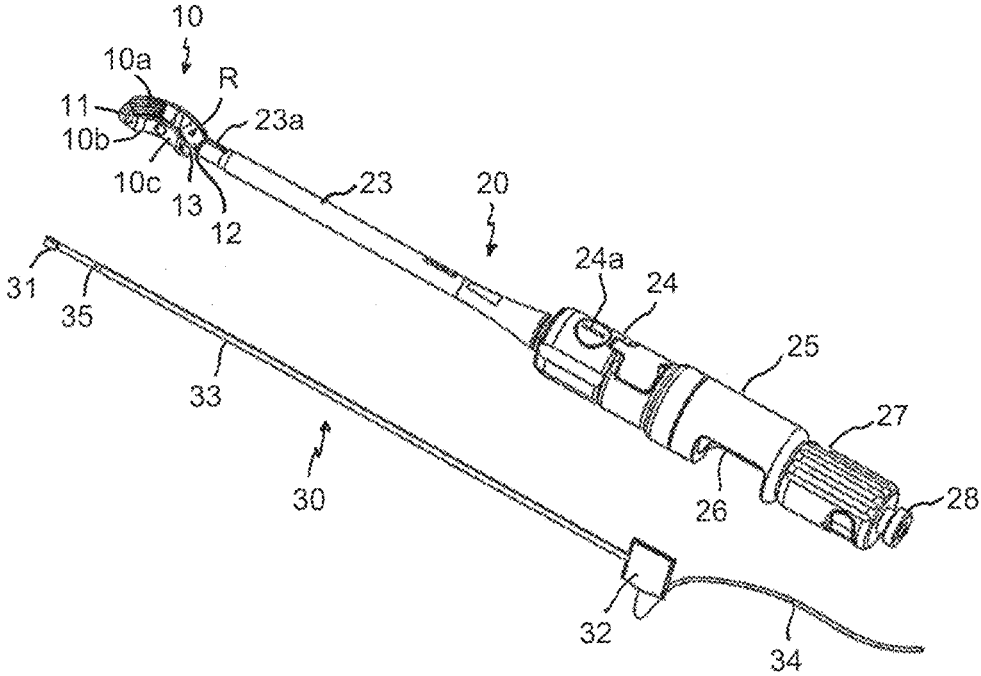
FIG. 1 shows a perspective exploded view of a system including an intervertebral implant and an instrument for inserting the intervertebral implant.
Figure 2:
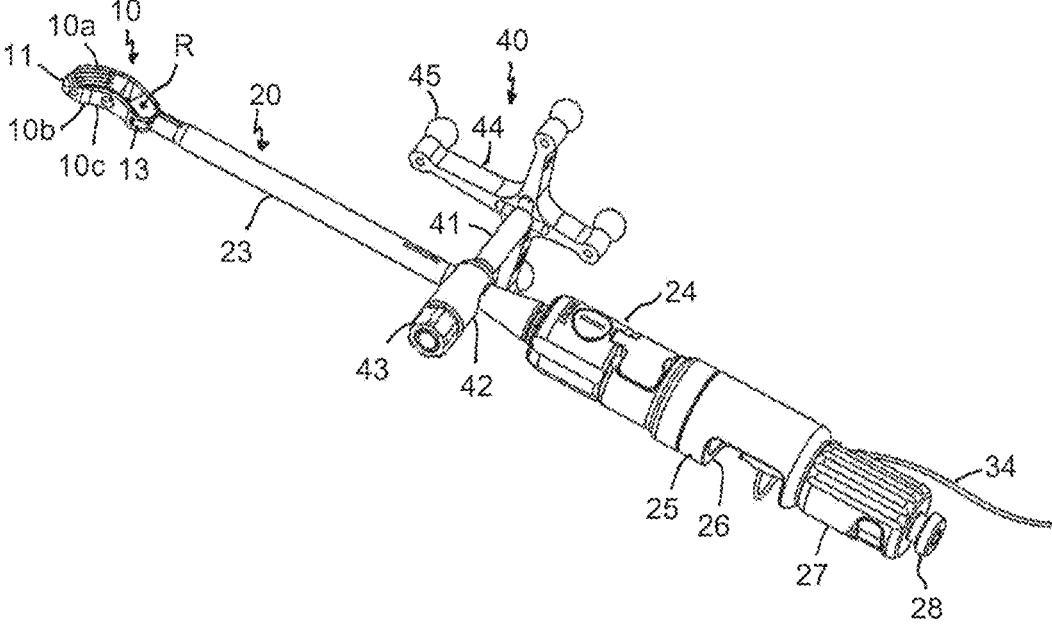
FIG. 2 shows a perspective view of the intervertebral implant and the instrument of FIG. 1 in an assembled state, and additionally with a navigation device attached to the instrument.
Figure 3:
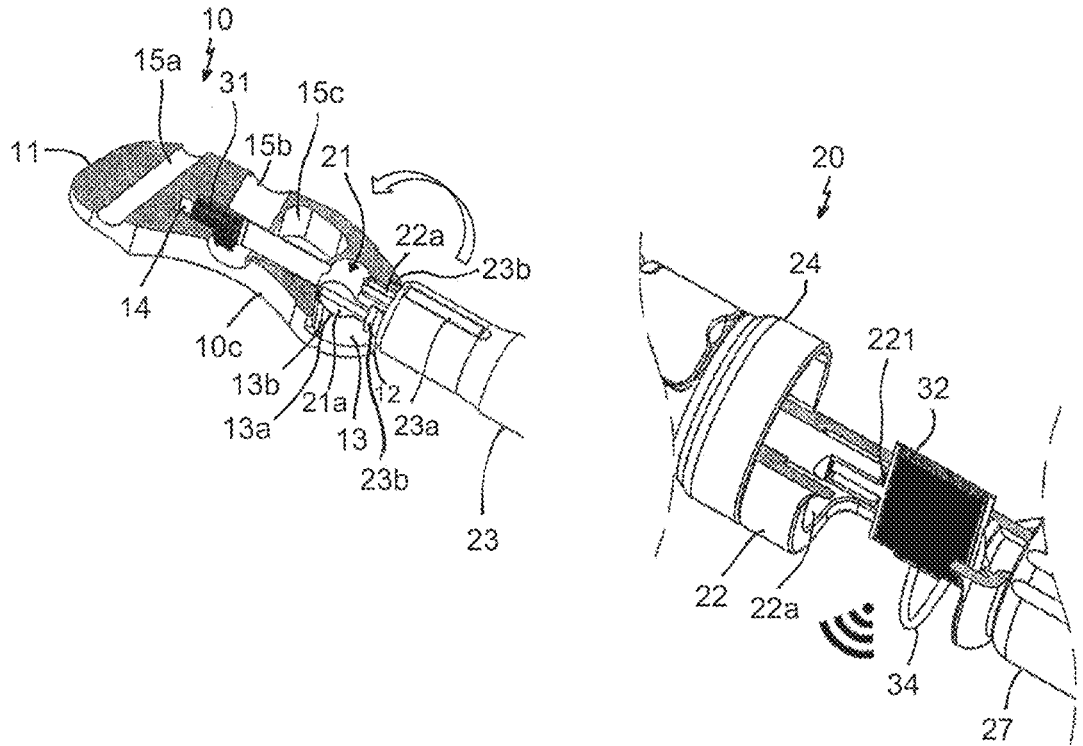
FIG. 3 shows a perspective view of portions of the system of the intervertebral implant and the instrument of FIG. 2, wherein cross-sections of portions of the intervertebral implant and of the instrument are shown.

Referring to FIGS. 1 to 3, an embodiment of a surgical implant for use in spinal or musculoskeletal surgery or in simulated surgery, in the form of an intervertebral implant 10, and an instrument 20 configured to facilitate insertion of the surgical implant are shown. The system includes a detection device 30 that is provided with a sensor 31 and a transmission portion 32 for transmitting data detected by the sensor 31 to an evaluation unit. The detection device 30 is configured to extend through the instrument such that the sensor 31 can be accommodated in the intervertebral implant 10.

The intervertebral implant 10 is formed as a body with a top wall 10*a* and an opposite bottom wall 10*b* that are configured to engage end plates of adjacent vertebrae when the intervertebral implant 10 is placed into an intervertebral space. A sidewall 10*c* connects the top wall 10*a* and the bottom wall 10*b*. The body has an outer contour adapted to fit into the intervertebral space, for example, the outer contour can have a banana shape or a kidney shape. However, any other suitable shape may also be realized. In view of its path of insertion, the intervertebral implant 10 has a first or leading end 11 and an opposite second or trailing end 12. At the trailing end 12, a recess 13 is formed that permits engagement with the instrument 20 in a manner such that the implant 10 can be pivoted relative to the instrument in a predefined angular range. In greater detail, the recess 13 defines an circumferentially extending opening for inserting an engagement portion 21 of the instrument 20. Internally, the recess 13 has a spherical portion 13*a* (also shown in FIG. 5) that is configured to accommodate a spherical portion of the engagement portion 21 of the instrument 20. Sidewalls 13*b* that limit the recess 13 form an angle with each other and thereby limit the pivoting of the intervertebral implant 10 relative to the instrument 20. An axis R extending through the spherical portion 13*a* of the recess and substantially perpendicular to a longitudinal axis S of the instrument 20 forms an axis of rotation or a pivot axis of the intervertebral implant 10 relative to the instrument 20. A virtual line extending from the leading end 11 to the trailing end 12 and intersecting the axis R of rotation defines a longitudinal axis L of the intervertebral implant 10. The pivot or rotation angle of the intervertebral implant 10 relative to the instrument 20 is defined as the angle that the longitudinal axis L of the intervertebral implant 10 forms with the longitudinal axis S or shaft axis of the instrument.

From the recess 13, an elongate recess 14 extends inside the intervertebral implant 10 up to a distance from the leading end 11. The recess 14 is configured to accommodate the sensor 31 and a portion of a connection line 33 that connects the sensor 31 with the transmission portion 32. For example, the recess 14 may have an elongate rectangular contour that has a width only slightly greater than that of the sensor 31, so that the sensor 31 is guided therein when the sensor is inserted into the intervertebral implant 10. A plurality of additional openings and/or recesses 15a, 15b, 15c may be formed in the body for various purposes, for example, to allow ingrowth of tissue and vessels, for saving weight, or for cleaning, among other purposes.

It shall be noted that the intervertebral implant can also be realized as a porous body or a body with a grid-like structure that exhibits an open cell structure.

The instrument 20 includes the engagement portion 21 forming an end portion of a shaft 22 that is guided in a sleeve or tube 23. The shaft 22 is advanceable and retractable relative to the tube 23 such that the shaft 22 can be advanced to engage the intervertebral implant 10, and can be retracted to fix the intervertebral implant 10 thereto. A longitudinal channel 22a extends through the shaft 22 and the engagement portion 21 for passing the detection device 30 therethrough. The length of the shaft 22 is such that an end portion 220 opposite to the engagement portion 21 extends out of the tube 23 to permit attachment of further parts and to permit the insertion of the sensor device 30. For insertion of the sensor device 30, the longitudinal channel 22a provides an insertion window 221 through which the detection device can be inserted.

The engagement portion 21 may be spherical segment-shaped with flat sidewalls 21a. In addition, the shaft 22 is at least partially rotatable relative to the tube 23. A size of the engagement portion 21 relative to the recess 13 is such that the engagement portion 21 can be inserted into the recess 13 only in a first orientation in which the flat sidewalls 21a face substantially towards the top face 10a and the bottom face 10b of the intervertebral implant 10, respectively. Moreover, after insertion, the size of the engagement portion 21 is such that the engagement portion 21 is prohibited from removal in a second orientation in which the flat sidewalls 21a are in a substantially upright position in which they may be substantially perpendicular to the top wall 10a and the bottom wall 10b.

The shaft 22 may also have a marking 22b close to the engagement portion 21 that indicates when the engagement portion is at the second orientation, that is the upright position of the engagement portion 21. When the marking 22b is aligned with a marking 23a on the outer surface of the tube 23, the upright position of the engagement portion 21 is indicated. Once inserted, when the engagement portion 21 engages the spherical portion 13a of the recess 13, the intervertebral implant 10 is pivotable relative to the instrument 20. The tube 23 includes projections 23b at its front end which serve for guiding the shaft 22 therebetween. Moreover the projections 23b serve for orienting the intervertebral implant 10 such that the engagement portion 21 is insertable into the recess 13 of the intervertebral implant 10 only in the first orientation of the engagement portion 21. In addition, the projections 23b are configured to inhibit tilting of the intervertebral implant 10 relative to the axis of rotation R in the second configuration of the engagement portion 21. The sensor 31 of the sensor device 30 is insertable into the intervertebral implant only in the second configuration of the engagement portion 21. To fixedly connect the intervertebral implant 10 to the instrument, the shaft can be retracted so that tube 23 presses against the implant and firmly clamps the engagement portion 21 within the recess 13. Furthermore, the tube 23 may have a holding portion 24 at its end opposite to the engagement portion 21. Also on the holding portion 24, an axially extending elongate indication mark 24a may be provided that is configured to indicate the fixed or locked configuration of the instrument 20 relative to the intervertebral implant 10.

A cover member 25 is connectable to the shaft 22. The cover member 25 may be sleeve-shaped and may include a circumferential window 26 that exposes the transmission portion 32 of the detection device 30. For example, the window 26 permits access to a plug-in connector, for example, a USB connector, and/or to guide out a data cable 34, or facilitates wireless data transmission. Lastly, a nut 27 may be mounted to the shaft 22, for example, screwed thereto on a thread 220a provided at the end portion 220 of the shaft 22. The nut 27 is built such that the nut can be hit to drive the intervertebral implant 10 into the intervertebral space. At the free end of the nut 27, a cylindrical peg or hook 28 may be provided that can be engaged, for example, by a claw, so that the instrument 20 can be withdrawn once the intervertebral implant 10 has been placed.

The sensor 31 is configured to detect a change of an angle between the intervertebral implant 10 and the instrument 20. More specifically, the sensor 31 detects the angle change between the longitudinal axis L of the intervertebral implant 10 and the shaft axis S of the instrument 20. The sensor 31 may be, for example, an acceleration sensor that detects an acceleration of a mass through a change in capacity of a capacitor, or a piezoelectric acceleration sensor that detects a change in pressure by acceleration of a mass. Alternatively, the sensor 31 may be realized by a gyroscope that detects the displacement of a resonance mass and its hanging following a Coriolis acceleration. Also gravitational sensors may be applied. In particular, the acceleration sensor, the gravitational sensor, or the gyroscope may be realized with micro-electro-mechanical systems (MEMS). Such MEMS are well-known and include spring-mass systems, wherein the springs and the mass are formed by miniaturized silicon structures, for example, by means of photolithography. The resolution of the sensor 31 used in the detection device 30 may be preferably between about $0.5°$ to $2°$, and more preferably, about $1°$.

An overall length of the detection device 30 may be such that the transmission portion 32 projects out of the holding portion 24 of the tube 23 when the sensor 31 is placed in the recess 14 of the intervertebral implant 10. The main part of the connection line 33 that extends through the shaft 22 may be a substantially stiff line, for example, a printed circuit board. In the region of the engagement of the engagement portion 21 with the intervertebral implant 10, the connection line includes a flexible portion 35 that allows for rotational movement between the intervertebral implant 10 and the instrument 20. The flexible portion 35 may be realized, for example, as a substantially flat cable, such as a ribbon cable. Also, the transmission portion 32 may include a printed circuit board on which a data-processing unit for pre-processing the measured data and a transmission unit for transmitting the data to an external evaluation unit are provided. Alternatively, the data-processing unit may already be included in the sensor 31. The transmission unit 32 may be configured to transmit the data via the cable 34 and/or to transmit the data in a wireless manner.

Referring to FIG. 2, the instrument 20 may be equipped with a navigation device 40 that enables detection of the position of the instrument relative to a reference position. In the embodiment, the navigation device is an optical navigation device. Such a navigation device is well-known in the art and may include an arm 41 that extends substantially transverse to the shaft axis S, and can be mounted via a mounting portion 42 that permits adjustments to the axial position of the arm 41 and any device attached thereto along the shaft axis and the circumferential position of the arm 41. This can be realized, for example, via a clamping screw that is actuated by a knob 43. From the end of the arm 41, a plurality of transverse branches 44 extend, usually in a cross-arrangement, that may be oriented substantially parallel to the shaft axis S and which may have various lengths. At the free ends of the branches 44, balls 45 are provided, respectively, that are oriented away from the shaft axis S. The balls 45 are configured to be detected optically via an optical detection unit, such as a camera.

Figure 4:
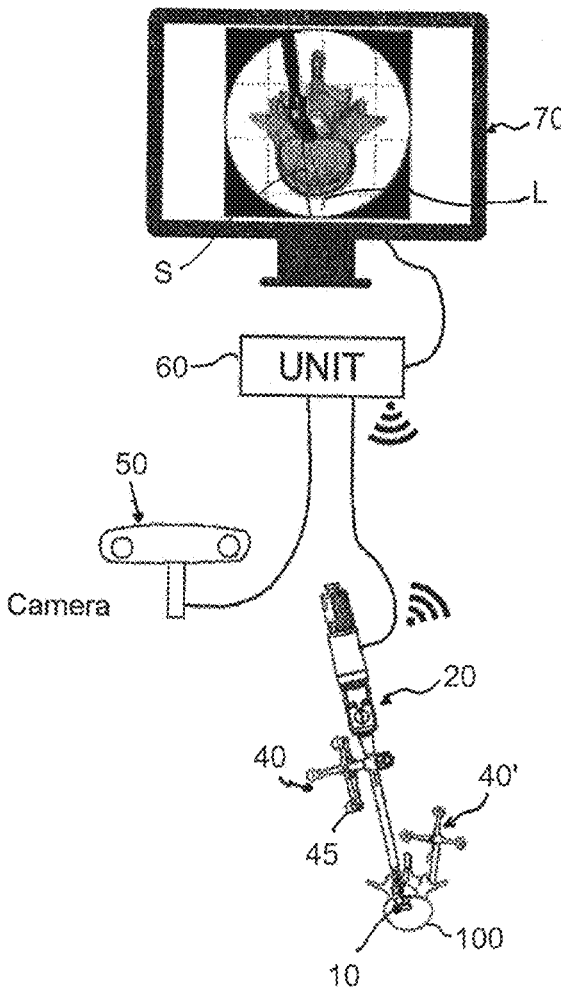
FIG. 4 shows a system including the intervertebral implant assembled with the instrument of FIGS. 1 to 3, a monitoring device, an evaluation unit, and a display.

Turning now to FIG. 4, a system or equipment for real-time visualization of the insertion of the intervertebral implant 10 is shown. A vertebra 100 is provided with a second navigation device 40' that may be of the same or similar type as the navigation device 40 attached to the instrument 20 and that may be mounted, for example, to the spinal process. The second navigation device 40' is detectable and delivers the position of the vertebra 100. The position of the instrument 20 is detectable via the navigation device 40 attached to the instrument 20. In addition, the equipment includes one or more cameras 50 to optically detect the position of the navigation device 40 on the instrument 10 and of the second navigation device 40' attached to the vertebra 100 so that the position of the instrument 20 relative to the vertebra 100 can be determined. The position of the intervertebral implant 10 relative to the instrument 20, and more specifically, the angle of rotation around the axis of rotation R, is detectable by the sensor 31. Thus the position of the intervertebral implant 10 relative to the vertebra 100 can be determined from the data obtained through the navigation device 40 and the data obtained by the sensor 31. The corresponding data are transmitted to a processing unit 60, such as a computer, that calculates image data that can be visualized on a screen 70. Hence, with this equipment, it is possible to display the procedure of placement of the intervertebral implant into the intervertebral space in a real-time manner.

Figures 5A, 5B, 6:
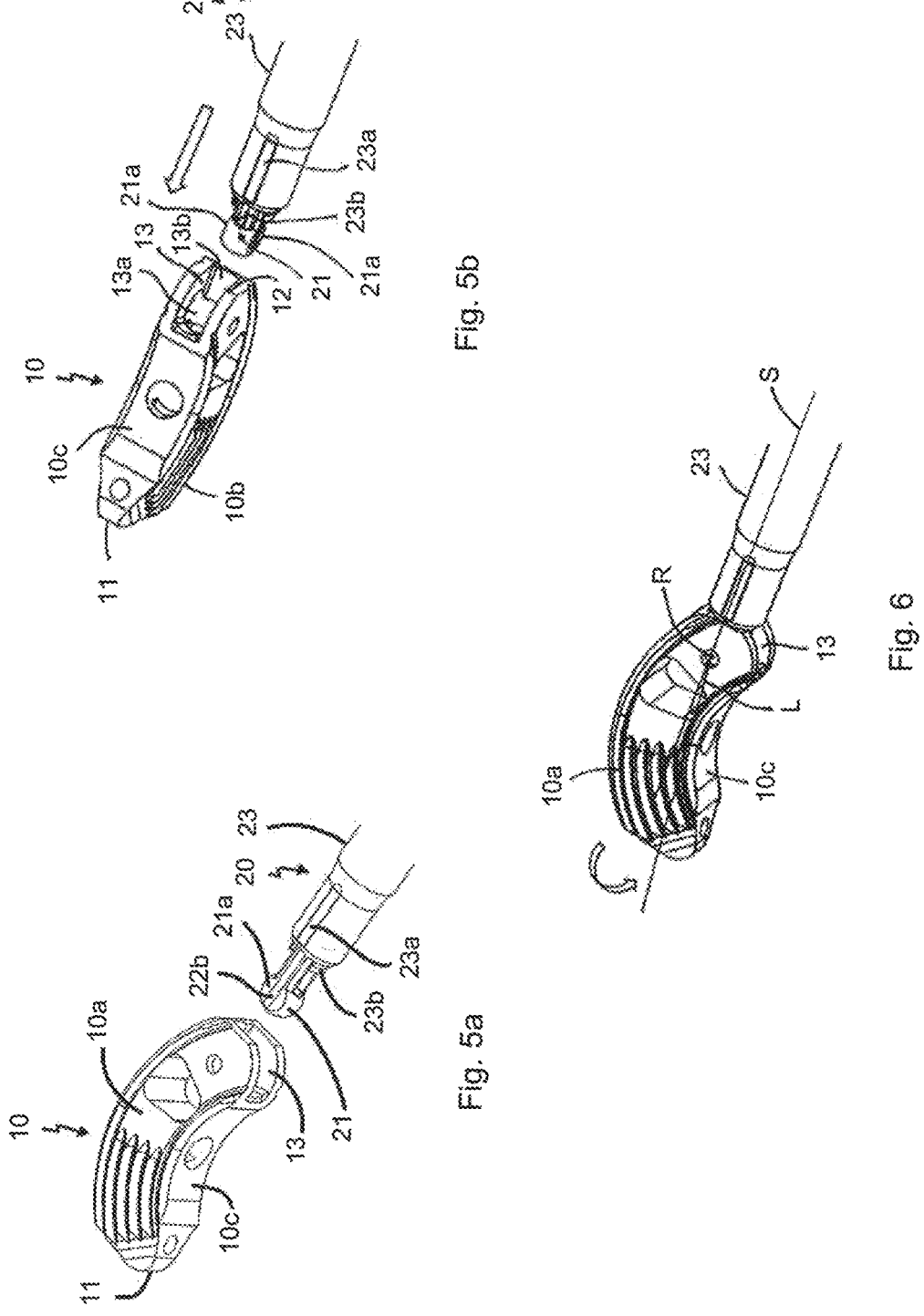
FIG. 5*a* shows an enlarged perspective view of a first step of mounting the intervertebral implant to the instrument according to a first embodiment.
FIG. 5*b* shows an enlarged perspective view of a first step of mounting the intervertebral implant to the instrument according to a second embodiment.
FIG. 6 shows the intervertebral implant and the front portion of the instrument of either FIG. 5*a* or FIG. 5*b* after mounting.

Referring to FIGS. 5a to 9, steps of assembling the instrument 20, the intervertebral implant 10, and the detection device 30 will be explained. FIGS. 5a and 5b show two alternative ways of attaching the instrument to the implant. As shown in FIGS. 5a and 5b, the intervertebral implant 10 is attached to the instrument 20 in a configuration in which the shaft is advanced relative to the tube and the engagement portion 21 is oriented such that the flat top and bottom surfaces 21a are substantially parallel to the top and bottom surface 10a, 10b of the intervertebral implant. In this configuration, the engagement portion 21 can be introduced into the recess 13. Then, the engagement portion 21 (FIG. 5a) or the intervertebral implant 10 (FIG. 5b) is rotated by 90°, so that the engagement portion 21 is seated with its spherical outer surface in the spherical recess portion 13a and is no longer removable. In a first method of attachment shown in FIG. 5a, marking 22b on the shaft 22 and marking 23a on the tube 23 are aligned, and engagement portion 21 is inserted into recess 13 of implant 10. After insertion, engagement portion 21 is rotated by 90° to be seated in the spherical recess portion 13a of recess 13 in an orientation where engagement portion 21 is prevented from being removed from recess 13. In an alternative second method of attachment shown in FIG. 5b, engagement portion 21 is already rotated by 90° prior to insertion into implant 10, compared to FIG. 5a. Here, the implant is also rotated by 90° compared to FIG. 5a, to align flat top and bottom surfaces 21a with top and bottom surfaces 10a, 10b of the implant 10. After engagement portion 21 is inserted into recess 13 in FIG. 5b, the engagement portion 21 maintains a same rotational orientation, while the implant is rotated by 90° instead, in order to engage engagement portion 21 with spherical recess portion 13a. In this manner, if the beginning orientation of the tool is as shown in FIG. 5b, then the sleeve 22 can be held at a constant rotational orientation relative to tube 23, and does not need to be rotated in order to connect to implant 10, which may be advantageous in some situations.

As shown in FIG. 6, the shaft 22 of the instrument may be at the outermost position of the recess 13. Then the shaft 22 is retracted so that the tube 23 is pressed against the intervertebral implant 20 to fixedly connect the intervertebral implant 10 to the instrument 20. The angle that the longitudinal axis L of the intervertebral implant 10 and the shaft axis S form is designated as a starting or initial angle, which may be substantially coaxial or 0° as shown, for example, in FIG. 6.

Figures 7, 8, 9:
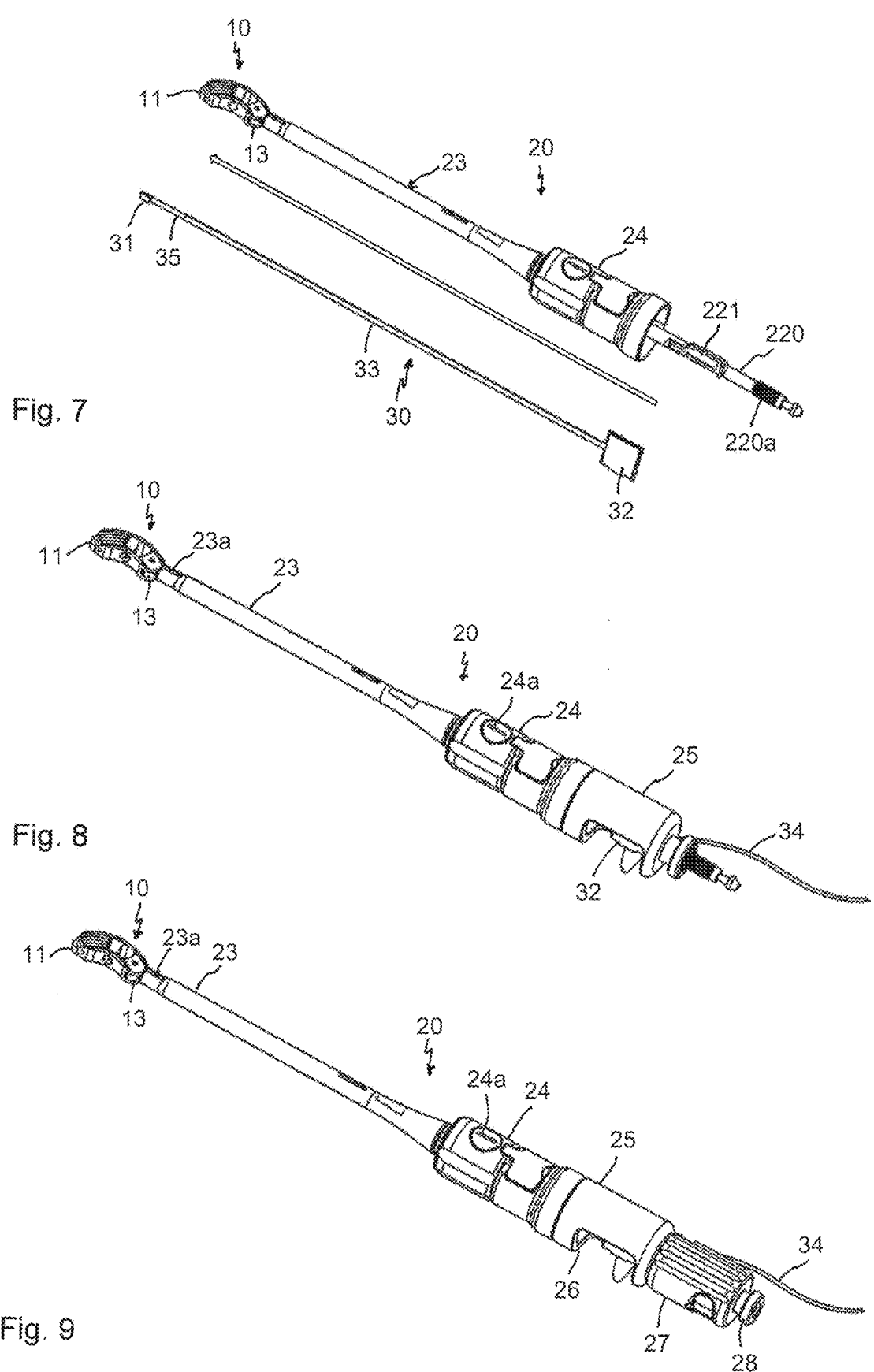
FIG. 7 shows a step of mounting a detection device to the intervertebral implant and the instrument.
FIG. 8 shows a perspective view of a step of attaching a securing nut to the assembly including the intervertebral implant and the instrument with the mounted detection device.
FIG. 9 shows a step of mounting an end portion to the instrument shown in FIGS. 7 and 8, where the end portion can be used for driving the intervertebral implant into the intervertebral space.

Next, as shown in FIG. 7, the detection device 30 is mounted to the assembly including the intervertebral implant 10 and the instrument 20. The detection device is guided through the shaft 22 until the sensor 31 and the flexible portion 35 rest in the recess 14 in the intervertebral implant 10. The transmission portion 32 projects out of the shaft 22.

Then, as depicted in FIG. 8, the cover member 25 is placed onto the holding portion 24 of the instrument, so that only the transmission portion 32 is accessible through the window 26 and the rest of the detection device 30 is protected.

Finally, as shown in FIG. 9, the nut 27 is mounted to the end portion 220 of the shaft 22. In this condition, the assembly is ready for insertion into a patient's body.

Figures 10A, 10B, 10C:
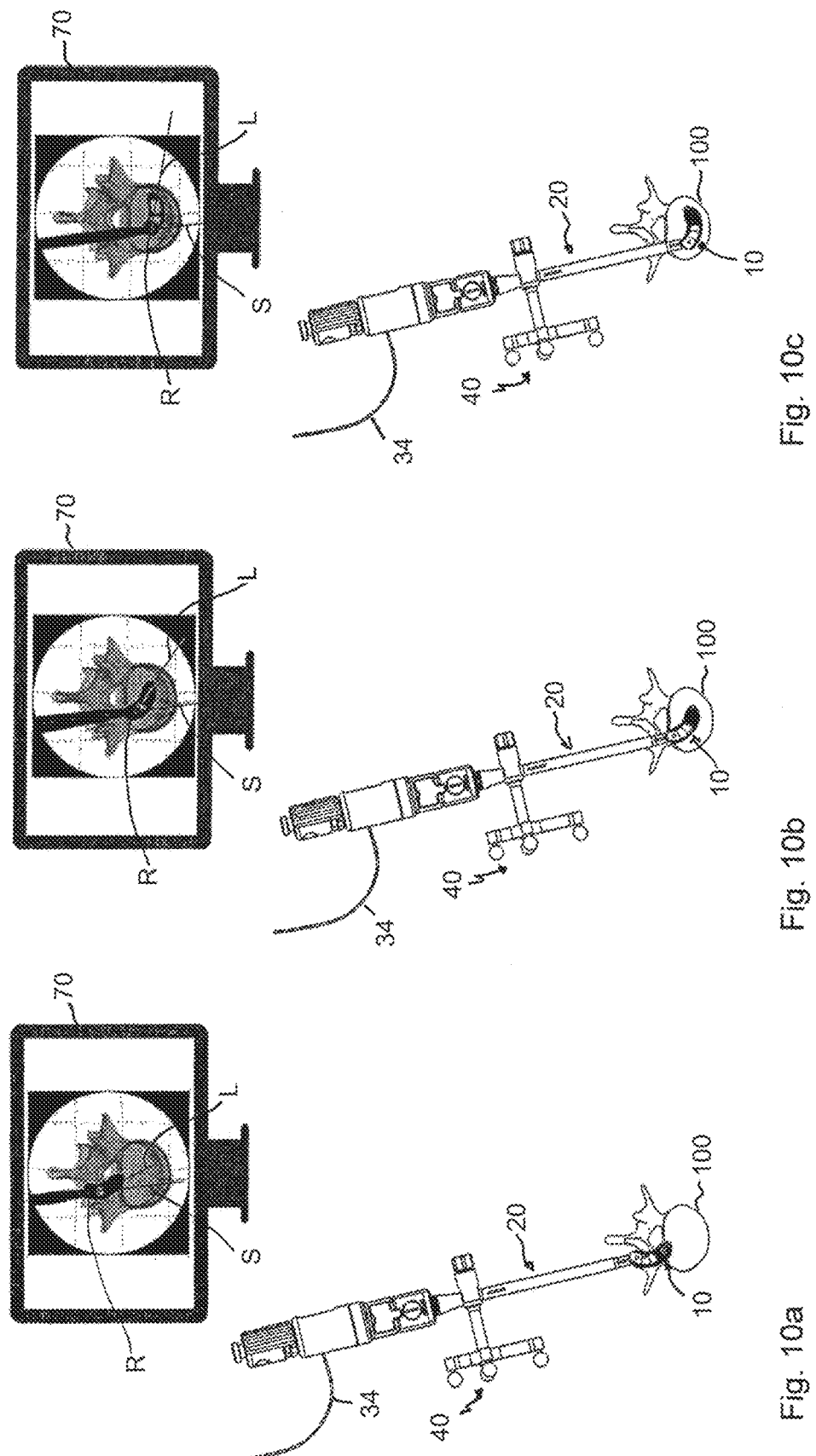
FIGS. 10*a* to 10*c* show steps of inserting the intervertebral implant into the intervertebral space along a curved trajectory while monitoring the position of the instrument and the angle of the intervertebral implant relative to the instrument.

Referring to FIGS. 10a to 10c, steps of insertion of the intervertebral implant 10 into the intervertebral space and the real-time visualization of the insertion are shown. It should be mentioned that, instead of the second navigation device 40' attached to a vertebra, any other reference position that may be outside the patient's body may be used for calculating the real-time position of the instrument 20.

As shown in FIG. 10a, the intervertebral implant is at the entrance of the intervertebral space while still being fixedly connected to the instrument 20. The angle between the intervertebral implant 10 and the instrument 20 in this condition may be the starting angle. The actual position of the intervertebral implant is calculated on the basis of geometrical data of the instrument 20, of the intervertebral implant 10, and of the vertebra 100. The position of the instrument is detected via the navigation device 40 and displayed in real-time on the screen 70.

Next, as shown in FIG. 10b, the fixation of the intervertebral implant 10 to the instrument 20 is released, for example, by retracting the tube portion 23 to an extent such that the implant is rotatable but the engagement portion 21 cannot be withdrawn from recess 13. In this condition, the intervertebral implant 10 can rotate or pivot relative to the instrument around the axis of rotation R, for example, in a pivot plane. Next, the intervertebral implant 10 is pushed into the intervertebral space with the instrument 20 and thereby rotates around the axis of rotation R. During this step, the angle of rotation of the implant relative to the instrument is, preferably constantly, detected and the data are transmitted via the transmission portion 32 to the processing unit 60. The software calculates, on the basis of the angular data and the absolute position data, the position of the intervertebral implant 10 relative to the vertebra 100. Thereby, the starting angle is used as an offset to the actually measured angle data. The insertion process can be displayed in real time on the screen 70. An image of the implantation site that may be obtained pre-operatively may be used to visualize the position of the instrument and the implant.

Finally, as depicted in FIG. 10*c*, the implant has reached its final implanted position. This may occur, for example, when a maximum angle between the intervertebral implant 10 and the instrument 20 is reached which is defined by the abutment of the shaft against the other sidewall 13*b* of the recess 13. However, due to the real-time visualization, the surgeon can see whether the placement of the intervertebral implant is correct even if the maximum angle is not yet reached.

After placement of the intervertebral implant 10, the connection between the intervertebral implant 10 and the instrument is released, for example, when the engagement portion is rotated by 90° and pulled out of the recess 13. The instrument can be removed, for example, by attaching claws to the peg 28 of the nut 27 to withdraw the instrument. Finally, by detaching the nut 27 and the cover member 25, the detection device 30 can be removed.

It shall be noted that in this embodiment, a change of the angle of the intervertebral implant relative to the instrument is detected in the pivot plane only. Using more than one sensor may permit adding more degrees of freedom for the determination of the position of the implant. It shall also be noted that different sensors may be used for different purposes and different implants, depending on the location where the implant is intended to be used.

Figure 11:
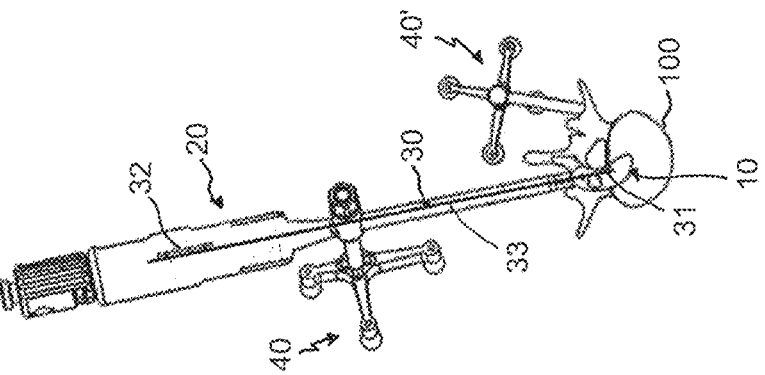
FIG. 11 shows a modified setup in which the intervertebral implant and the instrument according to FIGS. 1 to 10 is used together with a further navigation device.

Referring to FIG. 11, the same procedure as shown in FIGS. 10*a* to 10*c* can also be carried out with the second navigation device 40' attached to the vertebra 100, for example, to the spinal process.

Figure 12:
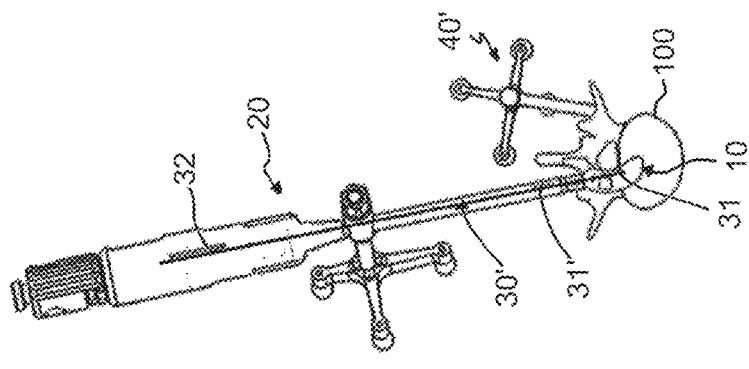
FIG. 12 shows a modified embodiment of the intervertebral implant and the instrument shown in the setup of FIG. 11, wherein a first detection device is provided in the intervertebral implant and a second detection device is provided in the instrument.

FIG. 12 shows a modification of the instrument. The detection device 30' includes a first sensor 31 which is identical or similar to the sensor 31 described before and which is configured to be placed in the intervertebral implant 10, and a second sensor 31' that is configured to be placed in the instrument. Both sensors 31, 31' may be connected to the same transmission portion 32. In this case, it is possible to permanently track the angular orientation of the implant 10 relative to the instrument 20, independently of whether the cage is fixedly connected to the instrument or is movable relative to the instrument.

Figure 13:
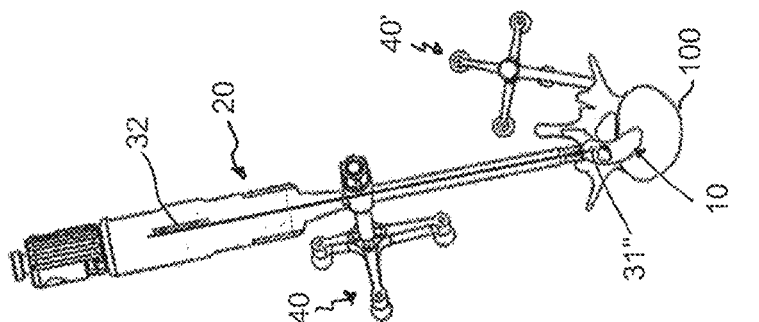
FIG. 13 shows a further modified embodiment of the intervertebral implant and the instrument shown in the setup of FIG. 11, wherein a detection device is provided in the axis of rotation.

FIG. 13 shows a still further modification in which, instead of the sensor 31 placed in the accommodation space of the intervertebral implant 10, a sensor 31", such as for example, a rotary encoder or another sensor as described above, is placed directly at the position of the rotational axis, for example, in the engagement portion 21. The sensor 31" also detects rotation of the instrument relative to the intervertebral implant.

Figure 14:
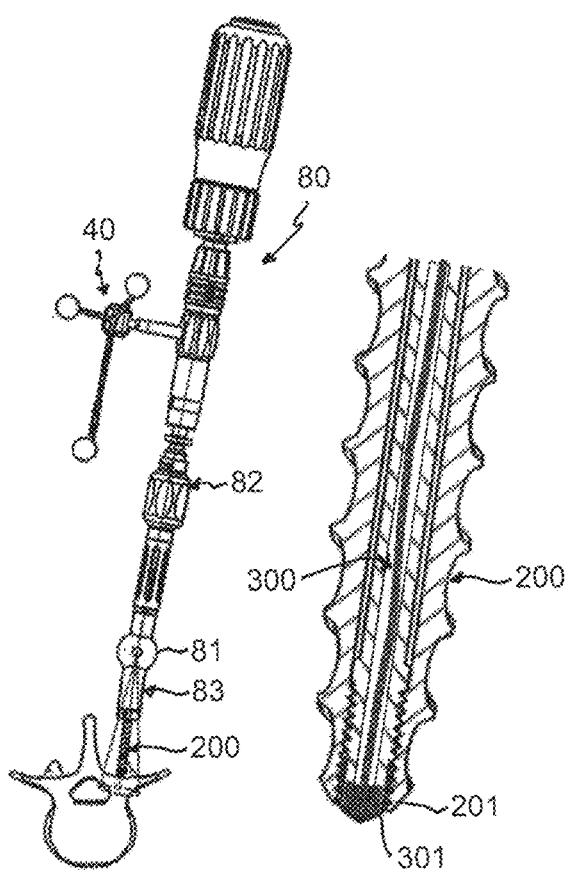
FIG. 14 shows a further embodiment of an implant in the form of a bone anchor and an instrument for inserting the implant, where a portion of the bone anchor with the detection device is shown in an enlarged cross-sectional view.

Referring to FIG. 14, a further embodiment of a device for use in spinal or musculoskeletal surgery is shown. The device is, in this case, an instrument in the form of a screw or shank inserter 80. The shank inserter 80 has a first component and a second component that is pivotable relative to the first component. This is realized, for example, via a cardanic joint or hinge 81, by means of which an upper shank inserter portion 82 that forms the first component and a lower shank inserter portion 83 that forms the second component are connected. The lower shank inserter portion 83 is configured to engage a head of a bone anchor 200 for inserting the bone anchor. On the upper shank inserter portion 82, a navigation device 40 as described before is attached. The shank inserter 80 and the bone anchor 200 have a channel for guiding through a detection device 300. The detection device includes a sensor 301 that is placeable within a tip 201 of the bone anchor 200. When the lower shank inserter portion 83 pivots relative to the upper shank inserter portion 82, the change of the angular position of the bone anchor 200 relative to the upper shank inserter portion 82 is detectable and traceable via computer-aided navigation, similarly as described before. This embodiment may be useful in applications where access to the location where the bone anchor is to be placed is restricted, and where pivoting of the shank inserter could facilitate easier insertion.

Figure 15:
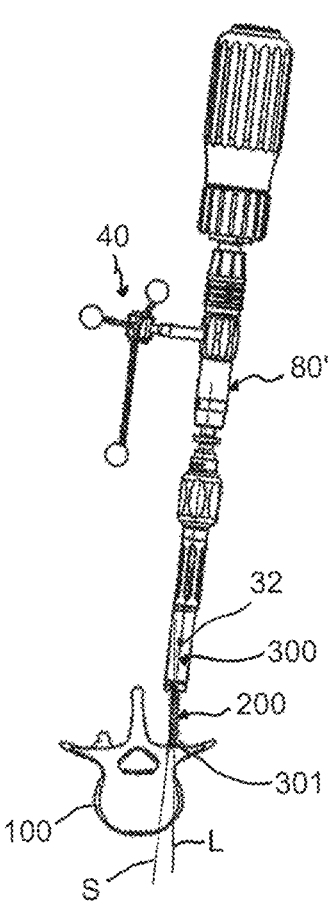
FIG. 15 shows a still further embodiment of an implant in the form of a bone anchor and an instrument for inserting the implant.

In FIG. 15, an embodiment including an instrument in the form of a shank inserter 80' and an implant in the form of the bone anchor 200 is shown that differs from the embodiment of FIG. 14 in that the shank inserter 80' does not have a pivotable portion. Instead, the shank inserter 80' is straight. The shank of the bone anchor 200 may assume during insertion, due to various reasons such as bending or specifically in the case of a bone anchor with flexible characteristics, an angle with respect to the longitudinal axis of the shank inserter 80'. The detection device 300 with the sensor 301 in the tip of the bone anchor 200 permits detection and tracking of the position of the tip 201 relative to the longitudinal axis of the shank inserter 80'.

Figures 16, 17:
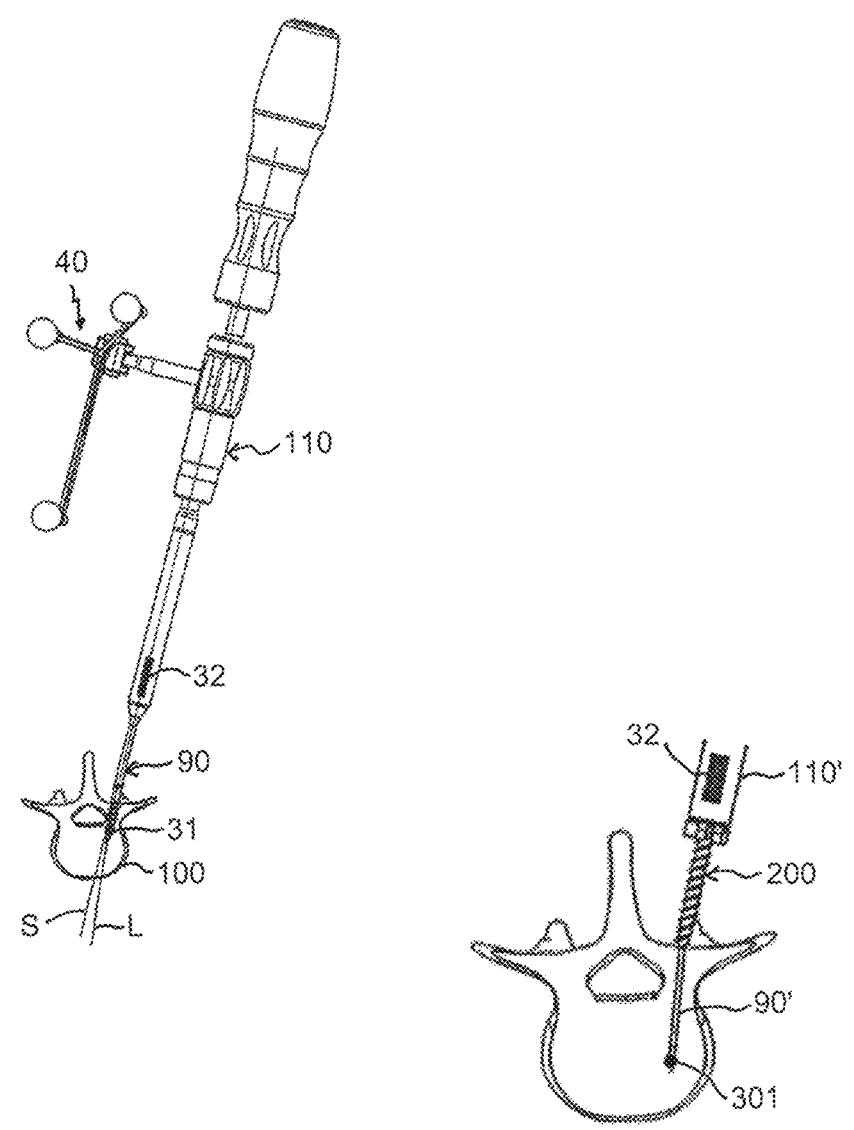
FIG. 16 shows a further embodiment of a surgical device with a first instrument component in the form of an awl or drill and a second instrument component in the form of an awl or drill holder.
FIG. 17 shows a still further embodiment of a surgical device with a first instrument in the form of an awl and a second instrument in the form of a shank inserter.

In FIG. 16, an embodiment of a surgical device is shown, with a first instrument component in the form of an awl or drill 90 and a second instrument component in the form of an awl or drill holder 110. The detection device includes a sensor similar to the previous embodiment, that is positionable in the awl or drill 90, preferably at the tip thereof. The navigation device 40 is provided at the awl or drill holder 110. With this surgical device, it is possibly to detect and track any deviation of the tip position of the awl or drill 90 from the shaft axis of the awl or drill holder 110 during insertion. Such a deviation may result, for example, from bending of the awl or drill 90.

In FIG. 17 an embodiment of a surgical device is shown with a first instrument in the form of an awl or drill 90' and a second instrument in the form of a shank inserter 110' that is configured to hold and insert a cannulated bone anchor 200 while the awl or drill 90' extends therethrough and is used for picking or pre-drilling a hole. A navigation device similar to the previous embodiment may be provided at the shank inserter 110'. The sensor device 301 in the tip of the awl or drill 90' permits detection and tracking of the position of the awl or drill 90' relative to the shank inserter 110', in particular, if the awl or drill 90' advances in an inclined or angled manner relative to the longitudinal axis of the shank inserter 110'.

Figure 18:
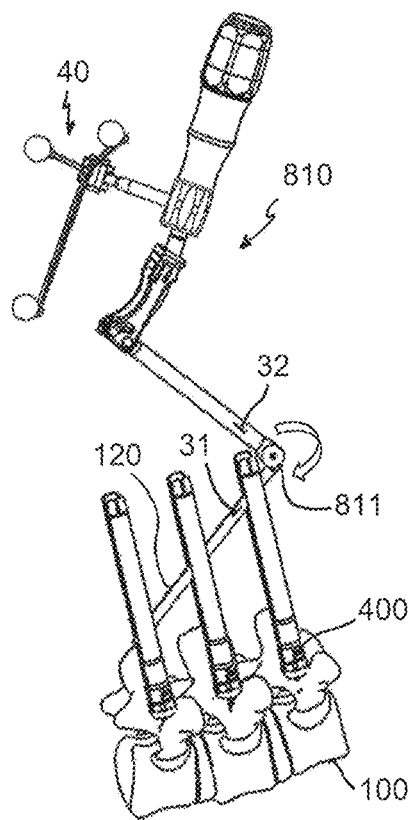
FIG. 18 shows a further embodiment of a surgical implant in the form of a spinal rod and an instrument in the form of a rod inserter.

In FIG. 18, an embodiment including a surgical implant in the form of a spinal rod 120 and an instrument in the form of a rod inserter 810 to insert the rod into receivers of bone anchors 400 is shown. The rod 120 is attachable to the rod inserter 810 at an attachment portion 811 that permits pivoting of the rod 120 relative to the rod inserter 810. The navigation device 40 is provided at the rod inserter 810. With a detection device including a first sensor at the rod 120 and optionally a second sensor at the rod inserter 810, similarly as described in previous embodiments, it is possible to detect and track the position of the rod 120 relative to the rod inserter 810, in particular, when the rod is pivoted relative to the rod inserter.

Figure 19A:
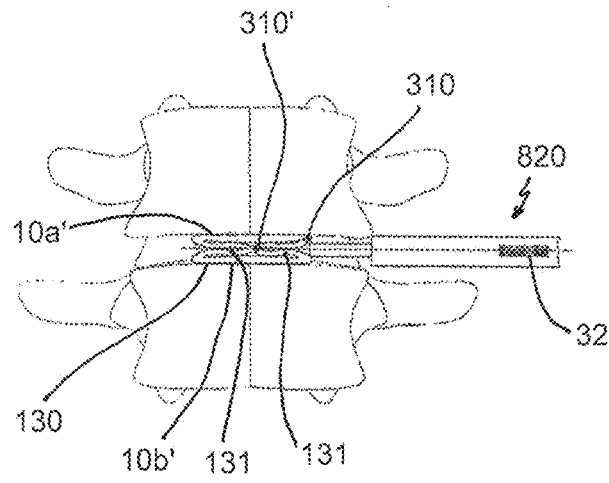
FIG. 19*a* shows a further embodiment of a surgical implant in the form of an expandable intervertebral implant and an instrument for insertion of the implant, wherein the implant is in a first, non-expanded configuration.
Figure 19B:
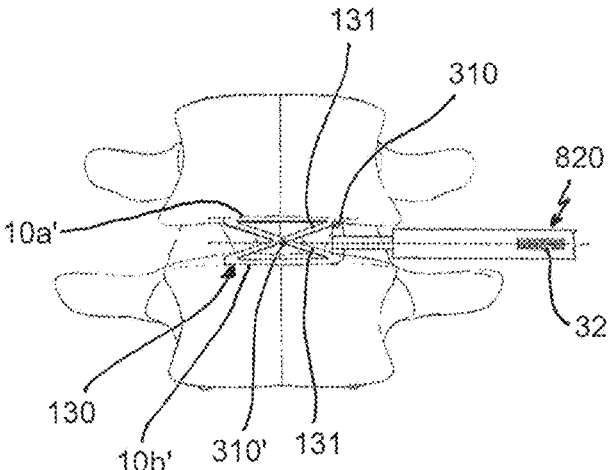
FIG. 19*b* shows the expandable intervertebral implant and the instrument of FIG. 19*a*, wherein the implant is in a second, expanded configuration.

FIGS. 19*a* and 19*b* show a still further embodiment including a surgical implant in the form of an expandable intervertebral implant 130 and an insertion and/or expansion instrument 820. The intervertebral implant 130 can assume a first configuration as shown in FIG. 19*a* in which the implant is collapsed and has a relatively smaller height, and a second configuration as shown in FIG. 19*b* in which the implant is expanded and has a greater height than in the first configuration. In greater detail, the intervertebral implant 130 includes a top wall 10*a*' and a bottom wall 10*b*' that are configured to engage adjacent vertebral end plates, respectively, and may have diagonal bars or struts 131 that cross each other and that may be resilient or may otherwise assume a compressed and an elevated or expanded configuration. A detection device may include a first sensor 310 that is positioned at an end of at least one of the struts 131 at or close to the top or bottom wall, and a second sensor 310' that may be positioned at the crossing section of the struts. With such sensors, a change in the position of the top or bottom wall 10*a*', 10*b*', in particular, when the height of the intervertebral implant 130 changes, can be detected and tracked. In addition, the instrument may include a navigation device similarly as described in previous embodiments.

Further modifications of the instrument or the other parts thereof may also be possible. In particular, the shapes of the various parts are not limited to the specific shapes shown in the embodiments. It is conceivable that the sensors can also be configured to detect other characteristics, such as temperature, pressure, bone density, etc.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An instrument for use in spinal or musculoskeletal surgery or in simulated surgery, wherein the instrument is not configured to be implanted into a human body and comprises: a first component having a first end, a second end, and a longitudinal axis extending between the first and second ends, wherein the first end comprises an engagement portion accessible from outside the instrument so as to be connectable to a surgical implant in an adjustable manner; and a detection device configured to monitor position changes of the surgical implant that is connected to the first end of the first component relative to the first component and to deliver position data corresponding to the position changes to an evaluation unit that is separate from the instrument, wherein the detection device comprises an extension that extends from the first end of the first component away from the first component in a direction of the longitudinal axis and a position sensor on the extension, wherein the position sensor is movable laterally away from the longitudinal axis to monitor movement of at least part of the surgical implant that is connected to the first end away from the longitudinal axis.

2. The instrument of claim 1, further comprising a navigation device positioned away from the first end of the first component and configured to deliver position data corresponding to a position of the instrument relative to the surgical site.

3. The instrument of claim 2, wherein the navigation device is an optical or electromagnetic navigation device.

4. The instrument of claim 1, further comprising a processor configured to deliver real-time image data corresponding to use of the instrument.

5. The instrument of claim 1, further comprising a second component connected to and adjustable relative to the first component.

6. The instrument of claim 1, wherein the position sensor is a first position sensor, and wherein the detection device further comprises a second position sensor positionable at the first component that is movable relative to the first position sensor to monitor the relative position and position changes of the first position sensor relative to the first component.

7. A system comprising the instrument of claim 1 and the surgical implant, wherein the instrument is configured to insert and/or adjust the surgical implant at an implant site.

8. The system of claim 7, wherein the detection device is configured to monitor rotation of the surgical implant relative to the first component around an axis of rotation that is transverse to the longitudinal axis.

9. The system of claim 7, further comprising a navigation device configured to deliver position data corresponding to a position of the instrument relative to the surgical site, wherein the position data delivered by the detection device and the position data delivered by the navigation device are both utilized to determine the position changes of the surgical implant relative to the first component.

10. The system of claim 7, wherein the surgical implant has an attachment surface connectable to the instrument and an accommodation space, and wherein the detection device is configured to detect a position of the surgical implant relative to the instrument, with at least part of the detection device being removably positionable in the accommodation space of the surgical implant.

11. The system of claim 7, wherein the surgical implant is rotatable relative to the instrument around an axis of rotation that is transverse to the longitudinal axis, and wherein the detection device is configured to detect an angle of rotation of the surgical implant around the axis of rotation relative to the instrument.

12. The system of claim 7, wherein the detection device comprises a transmitter for transmitting the position data to the evaluation unit and/or a processor for processing the position data.

13. The system of claim 12, wherein the transmitter is located on the instrument.

14. The system of claim 7, wherein when the surgical implant is connected to the instrument, the surgical implant is configured to assume a first configuration where the surgical implant is fixedly connected to the instrument, and a second configuration where the surgical implant and the instrument are movable relative to each other.

15. A method of performing a spinal or musculoskeletal surgical procedure or a simulated surgical procedure using an instrument that is not configured to be implanted into a human body and a surgical implant that is configured to be implanted into the human body, the instrument comprising a first component and a detection device, the first component having a first end, a second end, and a longitudinal axis extending between the first and second ends, wherein the surgical implant is connectable to an engagement portion that is accessible from outside the instrument at the first end of the first component in an adjustable manner, the method comprising:

monitoring position changes of the surgical implant relative to the first component with the detection device when the surgical implant is connected to the first end of the first component, wherein the detection device is further configured to deliver position data corresponding to the position changes to an evaluation unit that is separate from the instrument, wherein the detection device comprises an extension that extends from the first end of the first component away from the first component in a direction of the longitudinal axis and a position sensor on the extension, wherein the position sensor is movable laterally away from the longitudinal axis to monitor movement of at least part of the surgical implant away from the longitudinal axis; and using the position data to further adjust the position of the first component and/or the surgical implant.

16. The method of claim 15, wherein the method further comprises detecting a position of at least one of the first component or the surgical implant relative to a reference position via computer-aided navigation.

17. The method of claim 15, wherein the instrument further comprises a second component that is adjustable relative to the first component.

18. The method of claim 15, wherein the instrument is configured to prepare an implant site prior to advancing the surgical implant to the implant site.

19. The method of claim 17, wherein the second component is configured to directly connect to the surgical implant to insert and/or manipulate the surgical implant at an implant site.

20. The method of claim 15, wherein the instrument is configured to implant the surgical implant at an implant site, and wherein the position data is used to adjust the position of the surgical implant at the implant site.

* * * * *